United States Patent [19]

Cartmell et al.

[11] Patent Number: 4,653,501
[45] Date of Patent: Mar. 31, 1987

[54] MEDICAL ELECTRODE WITH REUSABLE CONDUCTOR

[75] Inventors: James V. Cartmell, Kettering; William E. Storms, Centerville, both of Ohio

[73] Assignee: Baxter Travenol Laboratories, Inc., Deerfield, Ill.

[21] Appl. No.: 853,023

[22] Filed: Apr. 17, 1986

[51] Int. Cl.⁴ .............................................. A61B 5/04
[52] U.S. Cl. .................................... 128/640; 128/641
[58] Field of Search .................. 128/639–641, 128/783, 802

[56] References Cited

U.S. PATENT DOCUMENTS

| | | | |
|---|---|---|---|
| 4,265,253 | 4/1981 | Abraham | 128/798 |
| 4,270,543 | 6/1981 | Tabuchi et al. | 128/639 |
| 4,319,579 | 3/1982 | Cartmell | 128/640 |
| 4,331,153 | 5/1982 | Healy | 128/641 |
| 4,365,634 | 12/1982 | Bare et al. | 128/640 |
| 4,409,981 | 10/1983 | Lundberg | 128/640 |
| 4,488,557 | 12/1984 | Engel | 128/635 |
| 4,490,005 | 1/1985 | Hovey | 339/278 C |
| 4,524,775 | 6/1985 | Rasmussen | 128/640 |

FOREIGN PATENT DOCUMENTS

US80/01606 6/1981 PCT Int'l Appl. .

Primary Examiner—Kyle L. Howell
Assistant Examiner—Randy Citrin
Attorney, Agent, or Firm—Roger S. Dybvig

[57] ABSTRACT

A disposable electrode pad is provided with a socket for a reusable electrode conductor attached to a lead wire. The pad includes a socket plate having a release coated top surface and overlying a frame having a bore filled with a gel matrix. The pad further includes a flexible clamp plate, part of which is strongly adhered to the frame and the rest of which is adhered to the release coated surface of the socket plate. The socket plate is provided with a bore used as a socket for a reusable, low profile electrode conductor which is fixedly attached to a lead wire having a jack for connection to external monitoring equipment. In use, the electrode pad is applied to the skin of a subject, the releasable part of the clamp plate is peeled away from the socket plate, the electrode conductor is inserted into the bore of the socket plate, and the clamp plate re-adhered to the socket plate in covering relation to the electrode conductor and the end of the lead wire attached thereto. Accordingly, the end of the lead wire and the electrode conductor are securely held in place relative to the gel matrix. Embodiments for both monitoring and stimulation purposes and alternative electrode conductor/lead wire embodiments are disclosed.

20 Claims, 11 Drawing Figures

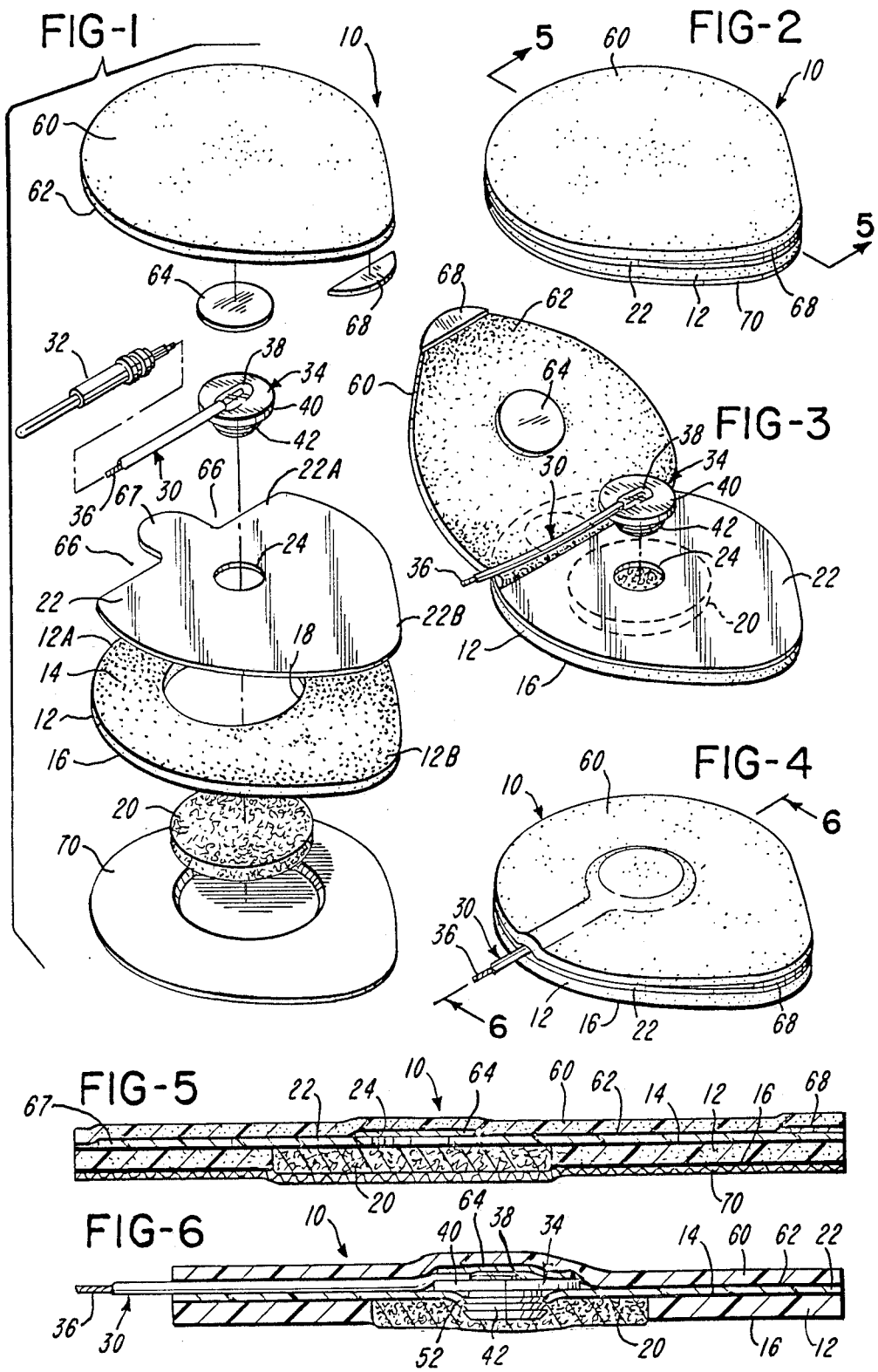

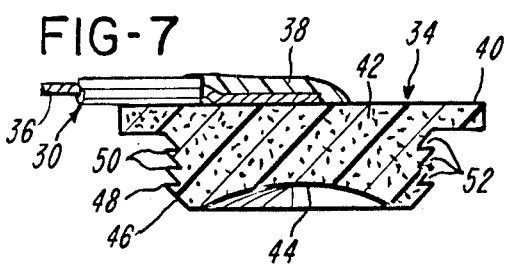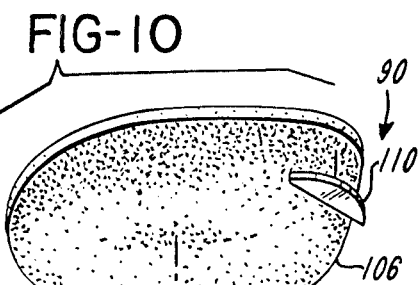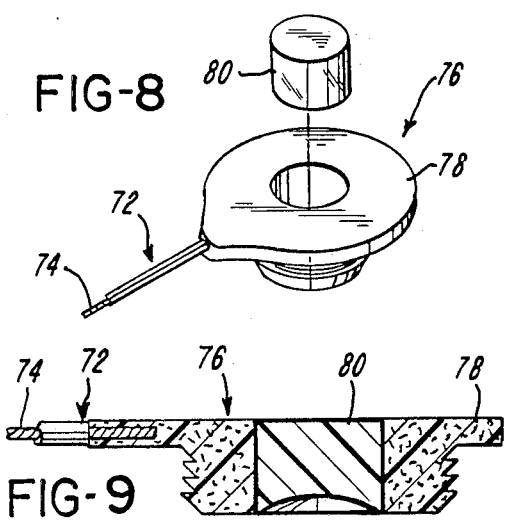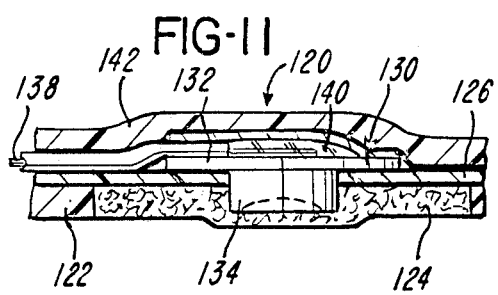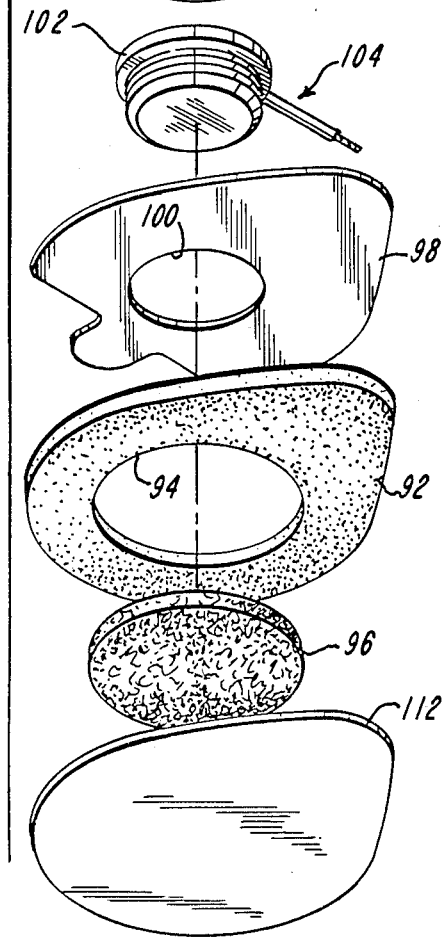

MEDICAL ELECTRODE WITH REUSABLE CONDUCTOR

SUMMARY OF THE INVENTION

The present invention relates to medical electrodes for transmitting electrical signals between the skin of a subject, such as a medical patient, and peripheral equipment for monitoring signals derived from the skin of the subject. This invention also relates to medical electrodes for applying stimulation signals to the skin of a subject.

There is a continuing need for high quality but inexpensive medical electrodes for ECG and related uses that reliably transmit signals to enable traces to be obtained that accurately represent signals produced by a patient's heart. For purposes of convenience and safety, such electrodes should be so inexpensive that it is practical to dispose of them after only one use. Accordingly, a primary object of this invention is to provide an inexpensive, high quality medical electrode.

One approach to providing inexpensive monitoring or ECG electrodes has been to provide a disposable electrode pad including an electrolyte and a carrier therefor and a reusable electrode conductor which is attached to a cable or lead wire used for connection to external monitoring equipment. It is generally recognized that, in order to obtain high quality traces, the portion of the electrode conductor engaged with the electrolyte should be a substantially pure metal, either substantially pure silver or a silver coated conductive plastic being preferred for ECG's taken with the patient at rest. For electrode applications in which signals are to be transmitted to the skin from external equipment, such as transcutaneous nerve stimulation (TENS) electrodes, the quality requirements of the conductor are not so high. For example, they may be made from conductive plastic or from lesser expensive metals such as stainless steel. Nevertheless, electrode conductors usually comprise the most expensive part of a medical electrode. By providing a reusable electrode conductor, substantial economies may be had because the more expensive conductor may be reused many times while the less expensive electrode pad is discarded after each use. This invention takes advantage of this approach and it is a further object of this invention to provide an improved, high quality electrode having an inexpensive and disposable electrolyte pad and reusable electrode conductor.

One of the important considerations in the construction of an electrode of the type having a reusable conductor is the manner in which the conductor is attached to the electrode pad. In practice, the electrode pads are adhered to the skin of a patient and the electrode conductors are thereafter connected to the pads. Such connections, and subsequent disconnections, should be readily made without causing discomfort to the patient. For long term monitoring applications, the electrodes should have a low profile to minimize the patient's discomfort and to enable the patient to roll over in bed with little likelihood of accidentally pulling off the electrode or disrupting the connection between the electrode lead wire and the electrolyte gel.

To obtain high quality traces, the connection should be sufficiently secure that the electrode conductor is held firmly engaged with the electrolyte. This is a particularly difficult problem with electrodes used for long term monitoring and also with electrodes used for stress testing wherein the patient is physically quite active. Therefore, it is a further object of this invention to provide a medical electrode of the type comprising a reusable conductor and a disposable electrode pad having an improved connection between the conductor and the electrode pad whereby the conductor can be easily and securely engaged with the electrolyte. A related object is to provide an inexpensive electrode that has a low profile with an electrode conductor-to-electrolyte connection sufficiently secure that the electrode may be satisfactorily and comfortably used for long term monitoring and stress testing applications as well as for less demanding applications.

In accordance with this invention, a medical electrode is provided having an electrode pad comprising a laminated assembly of a flexible, electrically non-conductive, foam plastic body or frame with a patient-contacting adhesive layer on its lower surface. The foam frame has a bore filled with an electrolyte gel matrix, preferably a conductive adhesive, a urethane hydrogel being the material of choice. The electrode pad further comprises an electrically non-conductive socket plate overlying the gel matrix and the foam body to which it is adhesively secured. The socket plate is provided with a socket for connection of an electrode conductor to external monitoring equipment. The socket preferably comprises a bore centrally located over the gel matrix. For reasons to be described, the socket preferably has a release coating on its top surface.

The electrode conductor has a low profile and is provided with a short shank adapted to be inserted into the bore in the socket plate. The conductor further includes a disc-like top plate adapted to overlie the portion of the socket plate surrounding the bore, so that it may be inserted into the bore of the socket plate and project only slightly above it. A reusable lead wire having a jack for connection to external monitoring equipment is attached to the top plate.

The lead wire may be adhered to or embedded in the top plate of the electrode conductor. For monitoring purposes, the entire electrode conductor may be made from a conductive plastic and coated with a silver paint or plating. A particularly low profile may be obtained by embedding the end of the lead wire into the edge of the conductor top plate. Rather than silver coating the entire conductor, a small silver plated plastic plug may be press fit within a bore in the conductive plastic body of the electrode conductor. For an electrode intended to be used for stimulation purposes, an uncoated conductive plastic electrode conductor is preferred. This would usually have a larger skin-facing area than a monitoring electrode.

Further in accordance with this invention, the laminated assembly forming the electrode pad includes an electrode conductor and lead wire clamp plate that comprises a flexible, electrically non-conductive, foam plastic sheet or body with a pressure sensitive adhesive layer on its lower surface. Part of the clamp plate is strongly adhered to the frame and the rest of the clamp plate is adhered to the release coated top of the socket plate. In use, the electrode pad is applied to the skin of a subject, the part of the clamp plate engaging the release coated socket plate is peeled away from the socket plate, the electrode conductor is inserted into the bore of the socket plate, and the clamp plate re-adhered to the release coated top of the socket plate in covering relation to the electrode conductor and the end of the lead wire attached thereto. Accordingly, the lead wire and the electrode conductor are securely held in place relative to the electrolyte.

The shank of the electrode conductor may be slightly oversized with respect to the bore of the socket plate and have ridges so constructed that the portions of the socket plate surrounding the bore tightly engage the conductor between the ridges to enhance the security of the connection between the electrode conductor and the socket plate. As an alternative, the shank may snugly fit within the bore of the socket plate and the electrode conductor will be held in place primarily by the clamp plate.

Other objects and advantages of this invention will become apparent from the following description and the drawings.

BRIEF DESCRIPTION OF THE DRAWINGS

FIG. 1 is an exploded perspective view of a medical electrode pad of this invention mounted on a release liner, a lead wire cable therefor, and an electrode conductor.

FIG. 2 is a perspective view of the electrode pad and the release liner of FIG. 1 prior to use.

FIG. 3 is a perspective view of the electrode pad of FIG. 1 shown with the clamp plate peeled back to permit attachment of the lead wire and the electrode conductor to the socket plate, the the lead wire being shown in fragmentary perspective and the electrode conductor being shown exploded from its socket.

FIG. 4 is a perspective view of the electrode pad of FIG. 1 as it would appear during use, with the the lead wire being shown in fragmentary perspective.

FIG. 5 is an enlarged, cross-sectional view of the medical electrode pad and the release liner taken on line 5—5 of FIG. 2.

FIG. 6 is an enlarged cross-sectional view of the medical electrode pad, a fragment of the lead wire, and the electrode conductor taken on line 6—6 of FIG. 4.

FIG. 7 is a greatly enlarged cross sectional view of the electrode conductor and a fragment of the lead wire.

FIG. 8 is an exploded perspective view of the electrode conductor and a fragment of the lead wire of a modification.

FIG. 9 is an enlarged cross sectional view of the electrode conductor and a fragment of the lead wire forming the modification of FIG. 8.

FIG. 10 is an exploded perspective view of a second embodiment of a medical electrode pad of this invention, a fragment of a lead wire therefor, and an electrode conductor.

FIG. 11 is a fragmentary cross-sectional view of a medical electrode pad, a fragment of the lead wire, and a third embodiment of an electrode conductor.

DESCRIPTION OF THE PREFERRED EMBODIMENTS

With reference to FIGS. 1 to 7, a medical electrode according to the present invention includes a disposable electrolyte carrier or electrode pad generally designated 10 which comprises a laminated assembly of a flexible, generally ring-shaped body or frame 12 having adhesive layers 14 and 16 on its upper and lower faces, respectively. The frame 12 is made from electrically non-conductive foam material and may comprise any of a wide variety of closed cell thermoplastic foams which are well known in the art, the material of choice for the present invention being a polyethylene foam. Adhesive layers 14 may be any suitable adhesive usable with the frame 12 and the layer 16 may comprise any conventional, electrically non-conductive pressure sensitive adhesive of the type generally known as "patient contact" adhesives which may be safely used to affix the electrode pad 10 to the skin of a patient.

The frame 12 has a circular bore 18 filled with a generally cylindrical matrix 20 of electrolyte gel, the gel matrix 20 preferably comprising a conductive adhesive and having a thickness greater than the frame 12. Various conductive adhesive materials may be used depending upon the application for which the electrode is intended. The material of choice for the present application is a urethane hydrogel which is of a gelatinous consistency and which contains an electrolyte in an amount sufficient to render it electrically conductive. The electrolyte comprises an ionizable salt compatible with the metal used to form the electrode conductor which will be described below. These are well known in the art; examples are the use of sodium chloride when the conductor is made from or coated with silver, as is presently preferred for monitoring purposes, and the use of sodium sulfate with stainless steel.

Alternate materials that may be used for the electrolyte include a commercially available conductive adhesive composition comprising karaya gum modified with sodium chloride, available from LecTec Corporation, 120 South Crosstown Circle, Eden Prairie, Minn. Various other conductive adhesive compositions that may be usable are described in the following U.S. Patents: Marks et al. U.S. Pat. No. 3,357,930; Kater U.S. Pat. No. 3,993,049; Berg U.S. Pat. No. 4,066,078; Hymes U.S. Pat. No. 4,125,110: Cross et al. U.S. Pat. No. 4,141,366: and Hymes U.S. Pat. No. 4,274,420. Whatever the composition of the conductive adhesive, it should be of the type which will adhere to the skin of a patient and will have a cohesive strength sufficient to substantially maintain its shape and to permit it to be peeled from the skin to which it is attached without leaving any appreciable residue.

The shape of the frame 12 is not critical to its function, except that, for most applications, the gel receiving bore 18 is preferably generally centrally located and completely surrounded by the frame 12 to avoid drying out of the electrolytic gel. The frame 12 shown in the drawing has a generally semi-circular "rear" portion 12A and a rounded triangular "front" portion 12B. This particular configuration is useful for purposes which will be described below.

Overlying the gel matrix 20 and the frame 12 is a socket plate 22 adhered to the frame 12 by the adhesive layer 14 on the upper surface of the frame 12. Socket plate 22 performs the functions of maintaining the shape of the electrode pad 10, of providing a covering for the gel matrix 20, and of providing a socket for connection of the electrode pad 10 to external monitoring equipment. The socket is in the form of a circular bore 24 extending through the socket plate 22 for the attachment of a reusable electrode conductor and lead wire as will be described below. Socket bore 24 has a substantially smaller diameter than the gel-receiving bore 18 in the frame 12. It is generally centrally located within the socket plate 22 and is coaxial with the center of the gel matrix 20. The socket plate 22 comprises a relatively stiff sheet of electrically non-conductive thermoplastic material such as styrene, vinyl, or polyethylene terephthalate (Mylar). In general, the socket plate 22 should be resiliently flexible but sufficiently stiff that it will firmly hold the electrode conductor within the socket 24 as will be described below. Mylar sheet having a thickness of approximately 4 or 5 mils or vinyl sheet of approximately 5 or 6 mils are examples of materials from which the socket plate 22 could be made. The top surface of the socket plate 22 has a release coating, such as a silicone, to render it partly resistant to adhesives for reasons which will become apparent.

A reusable lead wire, generally designated 30, is provided, having a jack 32 at one end and an electrode conductor 34 at its other end, and functions to transmit signals to or from the skin of a subject. Thus, the lead wire 30 has a conductive wire 36 jacketed by an insulating sleeve preferably made from silicone rubber or other adhesive-resistant material. A bare end of the wire 36 opposite the jack 32 is fixedly attached, as by an epoxy adhesive 38, to the electrode conductor 34. In the contemplated use of this invention, the electrode pad 10 will be discarded after each use, but the lead wire 30 and the electrode conductor 34 will be repeatedly used with like electrode pads.

With reference to FIG. 7, the electrode conductor 34 comprises a one piece body having a circular, disc-like top plate 40 and a short, generally cylindrical shank 42 depending centrally therefrom. Shank 42 is adapted to extend through and be retained by the socket plate bore 24 so that it becomes lodged in the gel matrix 20 as shown in FIG. 6. There it will be noted that the length of the shank is approximately the same as, or less than, the combined thicknesses of the frame 12 and the socket plate 22.

For monitoring purposes, it is preferred that the electrode conductor 34 comprise substantially pure silver or be plated or coated with substantially pure silver and that its outer surface be chlorided. Since low cost is important, the presently preferred electrode conductor for monitoring purposes comprises a nylon rendered conductive by inclusion of carbon that preferably has a silver coating, which may be painted or plated, at least along a portion of its surface that engages the gel matrix 20. It would also be possible to use a silver plated non-conductive plastic, such as ABS, but it is believed that such an electrode conductor may have a sufficient portion of its silver plating removed by abrasion resulting from repeated applications to the electrode pads that the continuity of the silver plating may be lost so quickly that the useful life of the electrode conductor would be unsatisfactorily limited. Other metals, such as stainless steel, could be used for short term monitoring, but silver provides the highest quality traces. A conductive plastic, such as the nylon material described above, could be used for stimulation electrodes by which signals are transmitted from external equipment to the skin of a patient.

Referring again to FIG. 7, the cylindrical shank 42 of the electrode conductor 34 illustrated therein has a concave bottom surface 44, a beveled lower outer wall 46 in the form of an inverted, truncated cone, sloping upwardly and outwardly from the bottom surface 44 that terminates at its upper end in a circular ridge or shoulder 48. Above the ridge or shoulder 48, there are plural additional circular ridges or shoulders 50 formed at the upper ends of each of plural body sections that also are in the form of inverted, truncated cones but which have a lesser height than the lower wall surface 46. Accordingly, the entire length of the shank 42 is provided with plural, closely-spaced, parallel ridges or shoulders 48 and 50 separated by plural circular grooves, designated 52.

The ridges or shoulders 48 and 50 have a diameter slightly greater, on the order of 0.010 to 0.020 inch, than the diameter of the socket bore 24. As an example, an electrode pad having a socket bore diameter of approximately 0.344 inch may be used with an electrode conductor having an outermost ridge diameter of approximately 0.355 inch.

Referring to FIGS. 1 to 5, the laminated assembly forming the electrode pad 10 further comprises a flexible top or clamp plate 60 having an adhesive layer 62 on its bottom surface. A release paper disc 64 is adhered to the center bottom of the clamp plate 60 in coaxial alignment with the bores 18 and 24. The clamp plate 60 is made from electrically non-conductive foam material and, for economy of manufacture, preferably comprises the same material from which the frame 12 is made. Clamp plate 60 preferably has the same size and the same outer marginal configuration as the frame 12 and is positioned on top of the socket plate 22 and the frame 12 so that its outer margin is coextensive or common with the outer margin of the frame 12. The socket plate 22 is somewhat smaller than the frame 12 and the clamp plate 60, so that parts of the frame 12 and the clamp plate 60, or more precisely their adhesive layers 14 and 62, are strongly adhered to one another.

In the particular embodiment illustrated in FIGS. 1-5, the outer margin of the front portion, designated 22B, of the socket plate 22 is coextensive or common with both the frame front portion 12B and the corresponding portion of the clamp plate 60, but the outer margin of its rear portion, designated 22A is constructed to be spaced inwardly from, i.e., closer to the axis of the bores 18 and 24, than the corresponding outer margins of the frame rear portion 12A and the corresponding portion of the clamp plate 60. Accordingly, the extreme rear portions of the frame 12 and the clamp plate 60 are strongly adhered to one another. The shape of the socket plate 22 is not critical, but it is important that a substantial portion of the socket plate 22 extend to the common outer margin of the frame 12 and the clamp plate 22 to separate them, and that a portion, usually of lesser area than the latter portion, be effectively cut away so that the frame 12 and the clamp plate 60 are directly adhered to one another.

The rear portion 22A of the socket plate 22 is formed with notches 66 uncovering a substantial portion of the rear portions of the frame 12 and the clamp plate 60. The notches 66 are separated by a boss 67 that does not extend to the outer margin of the frame 12 and the clamp plate 60 so that the entire rear portions of the frame 12 and the clamp plate 60 are strongly adhered to one another. A small paper finger tab 68 is adhered to the extreme front end of the adhesive layer on the bottom of the clamp plate 60 as a convenience in lifting the clamp plate 60 from the socket plate 22, as described below.

Referring to FIGS. 2 and 5, the electrode pad 10 is mounted, as is conventional, on a release liner 70 that covers the adhesive layer 16 and the lower surface of the gel matrix 22 and from which the electrode pad 10 would be removed immediately prior to use. The release liner 70 may comprise a sheet of silicon coated paper, styrene, or the like, formed to the same outer marginal shape as the frame 12. The assembled electrode pad 10 and release liner 70 may be packaged along with several other electrode pads 10 mounted on release liners 70 for shipment and storage in a substantially air and moisture vapor impervious package or envelope, which may comprise a conventional plastic and metal foil laminate.

When an electrode pad 10 of this invention is to be used, it is stripped off the release liner 70 and pressed onto the skin of a patient to which it is adhered, primarily by the adhesive layer 16 on the bottom of the frame 12 and also by the inherent tackiness of the gel matrix 20. The clamp plate 60 is then peeled upwardly and rearwardly away from the socket plate 22, as shown in FIG. 3, to expose the socket bore 24 and to thereby permit insertion of the shank 42 of the electrode conductor 34 into the the area occupied by the gel matrix 20. Of importance at this time is the adhesion between the mutually contacting portions of the socket plate 22 and the clamp plate 60, which strongly resists complete removal of the clamp plate 60 from the frame 12. As a result, the clamp plate 60 bends or hinges where it overlies the rear edge portions of the socket plate 22 and remains adhered to the frame 12 as it is peeled back to expose the socket bore 24.

After the clamp plate 60 is peeled back as shown in FIG. 3, the electrode conductor 34 is inserted into the bore 24 of the socket plate 22 and the clamp plate 60 is then returned into overlying engagement with the front portion of the socket plate 22. The parts will then appear as shown in FIGS. 4 and 6, with the clamp plate 60 overlying the electrode conductor 34 and the adjacent end of the lead wire 30, which are effectively clamped between the socket plate 60 and the clamp plate 22. The release paper disc 64 is sufficiently large that it, and not the adhesive layer 62, engages the top of the electrode conductor 34. Here it may be noted that FIG. 6 shows the shank 42 inserted into the bore 24 of the electrode pad 10, but the electrode pad 10 is not shown applied to the skin of a patient. In practice, such would ordinarily not be done.

When the electrode is no longer needed, the clamp plate 60 is again peeled back so that the electrode conductor 34 may be removed from the socket bore 24. The electrode pad 10 may then be removed from the subject and discarded.

For proper operation, the clamp plate 60 should adhere to the socket plate 22 with a sufficient bond that the electrode conductor 34 and the adjacent end of the lead wire 30 will be firmly clamped between the socket plate 22 and the clamp plate 60 throughout the duration of the monitoring procedure. On the other hand, it should be reasonably easy to peel the clamp plate 60 off the socket plate 22. Those familiar with adhesives of the type used with medical electrodes will be aware that the adhesive layer 62 on the bottom surface of the clamp plate 60 and the release coating on the top surface of the socket plate 22 can be formulated and applied to achieve the desired adhesive strength between the socket plate 22 and the clamp plate 60. Also, the adhesive layer 62 should readily peel away from the underlying portion of the lead wire, which it will do if the lead wire jacket is made from silicone rubber or the like.

With reference to FIGS. 6 and 7, because the lowest ridge or shoulder 48 of the electrode conductor shank 42 has a diameter greater than the bore 24, the beveled lower outer wall 46 of the shank 42 pushes the margins of the socket bore 24 downwardly as the shank 42 is inserted therein. This is feasible because the socket plate 22 is resiliently flexible and because the electrode conductor shank 42 is only minimally larger than the bore 26. Ultimately, the ridge 48 passes the bore 24 and, due to the resiliency of the socket plate 22, the margin of the bore 24 is biased to enter the groove 52 immediately above the lowest shoulder 48. As shown in FIG. 6, when the electrode conductor 34 passes through the bore 24, it becomes intimately engaged with the gel matrix 20. The bottom surface 44 of the shank 42 is made concave to provide a pocket for receiving the gel. Accordingly, the distance by which the gel matrix 20 is displaced downwardly upon connection of the lead wire 30 in the electrode pad 10 is minimized.

It will be appreciated that the electrode assembly shown in FIGS. 4 and 6 has an extremely low profile, adding to the thickness of the electrode pad only the thickness of the conductor top plate 40, the lead wire 30 and the epoxy adhesive 38. Further, it is seen that the electrode assembly of FIGS. 4 and 6 meets all of the objects of the invention, and in general constitues an inexpensive, high quality electrode that is easily assembled and dissasembled, comfortable to use, and, because of its low profile and the clamping of the conductor 34 and the adjacent end of the lead wire 30, may reliably be used for both long term and stress monitoring applications and for other applications as well.

In the modification of FIGS. 8 and 9, a lead wire assembly 72 has a conducive wire 74 fixedly attached to an electrode conductor 76 by an insert molding process that embeds the end of the wire 74 in the edge of the top plate 78 of the electrode conductor 76. The electrode assembly of FIGS. 8 and 9 may be used with the electrode pad 10 of FIGS. 1–5. As apparent, the profile of this construction is even lower than the first described embodiment.

FIGS. 8 and 9 show another variation, in which the electrode conductor 76 comprises a hollow, generally cylindrical body made from conductive plastic in the bore of which a silver plated, non-conductive plastic plug 80 is inserted, the plug 80 providing proper contact to the gel matrix of the electrode pad.

FIG. 10 shows a medical electrode construction particularly adapted to transmit stimulation signals to the skin of a patient rather than transmit signals from the skin. Thus, the pad 90 has a frame 92 with a bore 94 filled with an electrolyte gel matrix 96 and a socket plate 98 with a bore 100 adapted to receive the shank of an electrode conductor 102 attached to a lead wire assembly 104. Overlying the socket plate 98 is a clamp plate 106 provided with a centrally located release paper member 108 and a paper finger tab 110. Prior to assembly, the electrode pad 90 may be mounted on a release liner 112. Except for the electrode conductor 102, the various parts of this embodiment may be made from the same materials and they cooperate in the same manner as the corresponding parts of the embodiment of FIGS. 1–7. One difference between this embodiment and the embodiment of FIGS. 1–7 is that the diameter of the shank of the electrode conductor 102 is substantially greater than the shank 42 of the first embodiment so that the electrode may be used to apply stimulation signals to a relatively large area of the patients skin. The bores 94 and 100, and the gel matrix 96 are correspondingly greater in diameter. In general, the entire pad 90 may have a larger skin-facing area to accomodate the larger electrode conductor. Another difference between this embodiment and the first embodiment is that the electrode conductor 102 may be made from a conductive plastic or from stainles steel or some other relatively inexpensive material, since the reliablity of a silver conductor is not needed.

FIG. 11 shows another embodiment of an electrode in accordance with this invention which may be constructed as either a monitoring or a stimulation electrode. Again, corresponding parts may be the same as previously described. Thus, the electrode of FIG. 11 comprises an electrode pad 120 having a frame 122, a gel matrix 124, a socket plate 126 with a bore receiving an electrode conductor 130 having a top plate 132 and a shank 134. The electrode conductor 130 is attached to a lead wire 138, such as by an adhesive 140. A socket plate 142 overlies the electrode conductor 130, the adjacent end of the lead wire 138 and the socket plate 122, and cooperates therewith in the same manner as described above in reference to FIGS. 1–5. The difference is that the electrode conductor shank 134 of this embodiment has a smooth, cylindrical configuration and simply snugly fits within the bore of the socket plate 126 so that, in use, the electrode conductor 130 will be held in place almost solely by the clamp plate 142.

From the foregoing description, it may be seen that inexpensive electrodes are provided that may be used for long term or short term monitoring applications, for stress testing, for rest testing, and, with modifications, for stimulation purposes. The electrodes may be also be made in small sizes for neonatal monitoring. Thus, this invention provides a medical electrode construction with nearly universal applications.

Although the presently preferred embodiment of this invention has been described, it will be understood that various changes may be made within the scope of the appended claims.

Having thus described our invention, we claim:

1. A medical electrode assembly comprising:
    a reusable lead wire assembly; and
    a disposable electrode pad having
        an electrolyte gel matrix,
        socket means overlying said gel matrix including means for connection of said lead wire assembly to said matrix,
        a flexible clamp plate overlying said socket means, said clamp plate covering said connection means,
        means releasably securing said clamp plate to said socket means so that said clamp plate may be peeled away from said socket means sufficiently to uncover said connection means, and
        means for retaining said clamp plate with the other parts of said pad when it is peeled away from said plate means.

2. The medical electrode assembly of claim 1 wherein said pad further includes a frame having a bore filled by said gel matrix, adhesive means securing said socket means to said frame, and wherein said retaining means comprises said adhesive means.

3. The medical electrode assembly of claim 2 wherein said means releasably securing said clamp plate to said socket means comprises an adhesive on the surface of said clamp plate facing said socket plate, and wherein said retaining means further comprises said adhesive.

4. The medical electrode assembly of claim 1 wherein said socket means comprises a plastic socket plate having a socket therein overlying said gel matrix.

5. The medical electrode assembly of claim 4 wherein said lead wire assembly comprises a lead wire and electrode conductor means fixedly attached to said lead wire for engaging said gel matrix.

6. The medical electrode assembly of claim 5 wherein said electrode conductor means has a shank and wherein said socket comprises a bore extending through said socket plate through which said shank is releasably inserted into engagement with said gel matrix.

7. The medical electrode assembly of claim 6 wherein said pad further includes a frame having a bore filled by said gel matrix, adhesive means securing said socket means to said frame, and wherein said retaining means comprises said adhesive means.

8. The medical electrode assembly of claim 7 wherein said means releasably securing said clamp plate to said socket means comprises an adhesive on the surface of said clamp plate facing said socket plate, and wherein said retaining means further comprises said adhesive.

9. The medical electrode assembly of claim 5 wherein said electrode conductor has a disc-like top plate and a shank depending from said top plate, said lead wire being connected to said top plate; and wherein said socket comprises a bore extending through said socket plate through which said shank is releasably inserted into engagement with said gel matrix.

10. The medical electrode assembly of claim 9 wherein said lead wire comprises a conductor fixedly attached to said top plate by adhesive.

11. The medical electrode assembly of claim 9 wherein said lead wire comprises a conductor embedded in an an edge of said top plate.

12. The medical electrode assembly of claim 9 wherein said electrode conductor comprises a conductive plastic body.

13. The medical electrode assembly of claim 12 wherein said conductive plastic body has a bore extending therethrough and said electrode conductor further comprises a silver plated non-conductive plastic means press fit within said bore for engaging said gel matrix.

14. The medical electrode assembly of claim 12 wherein said conductive plastic body has a silver coating.

15. The medical electrode assembly of claim 9 wherein said pad further includes a frame having a bore filled by said gel matrix, adhesive means securing said socket means to said frame, and wherein said retaining means comprises said adhesive means.

16. The medical electrode assembly of claim 15 wherein said shank has a length approximately equal to the combined thicknesses of said socket plate and said frame.

17. For use with a reusable electrode conductor, a disposable medical electrode pad comprising an electrolyte gel matrix;
    a socket plate overlying said gel matrix, said socket plate comprising a sheet of plastic having a socket therein overlying said gel matrix for receiving an electrode conductor, said socket comprising a bore extending through said socket plate;
    a clamp plate overlying said socket plate and covering said bore;
    means releasably securing said clamp plate to said socket means so that said clamp plate may be pulled away from said socket plate sufficiently to uncover said bore; and
    means for retaining said clamp plate with the other parts of said pad when it is pulled away from said plate means.

18. The electrode pad of claim 17 further comprising a frame having a bore filled by said gel matrix, said retaining means comprising means for securing said clamp plate to said frame, and means securing said socket plate to said frame.

19. The electrode of claim 18 wherein said frame comprises a sheet of flexible foam plastic.

20. The electrode of claim 18 wherein said frame has a patient-contacting adhesive on its surface opposite its surface facing said socket plate.

* * * * *